United States Patent [19]

Aoyama et al.

[11] Patent Number: 5,385,890
[45] Date of Patent: Jan. 31, 1995

[54] ANTITHROMBIN III PREPARATION

[75] Inventors: Toshinobu Aoyama, Fukuoka; Keizo Hirahara, Iruma, both of Japan

[73] Assignee: Hoechst Japan Limited, Tokyo, Japan

[21] Appl. No.: 128,573

[22] Filed: Sep. 30, 1993

[30] Foreign Application Priority Data

Oct. 2, 1992 [JP] Japan ................... 4-264364

[51] Int. Cl.$^6$ ........................................... A61K 37/04
[52] U.S. Cl. ........................................ 514/21; 514/12; 422/102; 530/393; 436/17; 436/18
[58] Field of Search ............... 514/12, 21; 530/393; 422/102; 436/17, 18

[56] References Cited

U.S. PATENT DOCUMENTS

| | | | |
|---|---|---|---|
| 4,613,501 | 9/1986 | Horowitz | 424/89 |
| 4,841,023 | 6/1989 | Horowitz | 530/351 |
| 5,319,072 | 1/1992 | Uemura et al. | 530/393 |

OTHER PUBLICATIONS

"ICI Americas Products for Cosmeticse and Pharmaceuticals", ICI Americas Inc., pp. 24–25 and 28, 1977.
"Tween 80 Information Sheet".
Neugebauver, "A Guide to the Properties & Uses of Detergents in Biology and Bichemistry," Hoechst Corporation, 1987.
The U.S. Pharmocopeia, NF XVII, pp. 1967–1968, USP XXII, pp. 1763 and 1857.
Krantz et al., Bulletin of School of Medicine, University of Maryland, vol. 36, pp. 48–56, 1951.
Midori Juji K.K., "Antithrombin Agent and Its Preparation", Patent Abstracts of Japan, C Section, vol. 3, No. 114, Sep. 21, 1979, p. 144, C59, No. 54-95715.
H. J. Kolde "Polyethylene Glycol Can Be Validly Omitted From Chromogenic Peptide Substrate Assay For Antithrombin III", Chemical Abstracts, vol. 105, No. 17, Oct. 27, 1986, p. 296, Abstract-No. 148571u.
H. Van Voorthuizen et al., "Improved Assay Conditions For Automated Antithrombin III Determinations With The Chromogenic Substrate S-2238", Chemical Abstracts, vol. 102, No. 13, Apr. 1, 1985, p. 288, Abstract-No. 108558b.

*Primary Examiner*—Michael G. Wityshyn
*Assistant Examiner*—C. Sayala
*Attorney, Agent, or Firm*—Finnegan, Henderson, Farabow, Garrett & Dunner

[57] ABSTRACT

An antithrombin III is described comprising a lyophilized powder of antithrombin III and a polyoxyethylene glycol sorbitan alkyl ester as well as a kit composed of a container wherein a lyophilized powder of antithrombin III is placed and a solvent for the powder, characterized in that a polyoxyethylene glycol sorbitan alkyl ester is added to either or both of the powder and the solvent. The preparation has a high solubility in water by retaining its activity.

6 Claims, No Drawings

ANTITHROMBIN III PREPARATION

ANTITHROMBIN III PREPARATION

This invention relates to an antithrombin III preparation having an improved solubility. The invention is also related to a kit of that preparation.

Antithrombin III is useful for the treatment of disseminated intravascular coagulation (DIC) and defibrination syndrome, and is used in lyophilized form as a pharmaceutical preparation. For treatment, the lyophilized powder is dissolved in water before administration to patients. Lyophilized powders of antithrombin III, however, have a poor solubility in water and are inconvenient to use.

It is an object of this invention to provide a pharmaceutical preparation which comprises a lyophilized powder of antithrombin III having a high solubility in water. It is another object of the invention to provide a kit of that preparation.

A "lyophilized powder" is also to mean a "lyophilizate".

This invention is directed to an antithrombin III preparation which comprises a lyophilized powder of antithrombin III and a polyoxyethylene glycol sorbitan alkyl ester.

Moreover, this invention is also directed to a kit of an antithrombin III preparation comprising a container wherein a lyophilized powder of antithrombin III is placed and a solvent for the said powder, characterized in that a polyoxyethylene glycol sorbitan alkyl ester is added to either or both of the said powder and the said solvent.

The lyophilized powder of antithrombin III employed in this invention is not particularly limited and any of those produced according to conventional methods may be used. More specifically, one may use the blood fractions containing antithrombm III, e.g. human or animal blood serum, blood plasma and the like purified by any well-known purification methods such as the purification method using a heparin-crosslinked resin column and one may also use the antithrombin III obtained according to a genetic engineering technique.

The polyoxyethylene glycol sorbitan alkyl ester employed in the invention as a solubilizer for the antithrombin III is a member of class of non-ionic surface active agents and a safe substance approved to be employable for pharmaceutical preparations. TWEEN 20, TWEEN 40, TWEEN 60, or TWEEN 80, which are prepared by Atlas Powder Ca. (U.S.A.) and, for instance, sold by Wako Pure Chemical Industries, Ltd., may preferably be employed. "TWEEN" is a registered trademark. TWEEN 80 is particularly preferred. The amount of the said solubilizer employed is not critical and may usually be 0.04–20% (by weight), preferably about 2% for antithrombin III and usually 0.002–0.1% (w/v), preferably about 0.1% for the solvent (water).

The present preparation may be prepared by lyophilizing antithrombin III in the presence of the predescribed mount of the said solubilizer or by incorporating the prescribed amount of the said solubilizer into a lyophilized powder of antithrombin III.

The aforesaid kit of this invention may be prepared by combining a container in which the lyophilized powder of antithrombin III containing the solubilizer prepared according to the aforesaid method is placed with a container in which the solvent for antithrombin III is placed with or without the said solubilizer incorporated, or by combining a container in which the lyophilized powder of antithrombin III is placed with a container in which the solvent for antithrombin III containing the said solubilizer is placed. Vials may usually be employed as the container.

Where necessary, the present preparation may include fillers and other materials according to a conventional method for producing a pharmaceutical preparation.

According to this invention, there is provided an antithrombin III lyophilized powder preparation having an excellent solubility or a kit using the same. When the present preparation is dissolved in water and the resulting solution is suction-filtered, the time required for suction is 1/20 or less as compared with the prior art preparations. This means that in the present antithrombin III preparation the antithrombin III dissolves in water homogeneously and rapidly in the form of fine particles, which provides a solution with great practical usefulness in administrating antithrombin III. Moreover, the antithrombin III activity in the present preparation is not reduced and stable.

This invention will be more concretely explained by way of the following examples.

EXAMPLE 1

A lyophilized powder (50 mg) of antithrombin III derived from human plasma was dissolved in distilled water for injection (10 ml) containing 0.01% (w/v) of TWEEN 80 Wako Pure Chemical Industries, Ltd.). The solubility of antithrombin III was evaluated by suction-filtration of the resultant solution. The suction-filtration was performed at a suction pressure of 250 mmHg using a membrane filter (diameter 4 mm) with a pore size of 0.45 μm. The solubility was determined by the period of time required for filtration. A solution of the lyophilized powder of antithrombin III in 10 ml of distilled water for injection was used as a control. The results are shown in Table 1.

EXAMPLE 2

To a solution containing 50 mg of the antithrombin III derived from human plasma was added TWEEN 80 to a final concentration of 0.01% (w/v). Then, the mixture was lyophililzed, whereafter the lyophilized product was dissolved in 10 ml of distilled water for injection. The solubility was determined in the same manner as described in Example 1. The results are shown in Table 1. The figures shown in Table 1 are the mean values obtained by the results of the same tests repeated three times.

In Examples 1 and 2, the anticoagulant activity of antithrombin III before and after filtration was determined by using a commercially available kit (Behnngwerke A.G., Germany). No decrease of activity was noted.

TABLE 1

|  | Time required for filtration |
| --- | --- |
| No stabilizer | >30 minutes (Note 1) |
| Example 1 | 1 minute 48 seconds |
| Example 2 | 1 minute 29 seconds |

Note 1: Filtered volume in 30 minutes: 2.9 ml

We claim:

1. An antithrombin III preparation which comprises a lyophilized powder of antithrombin III and a polyoxyethylene glycol sorbitan alkyl ester.

2. The antithrombin III preparation according to claim 1 wherein the polyoxyethylene glycol sorbitan alkyl ester is "TWEEN 20", "TWEEN 40", "TWEEN 60" or "TWEEN 80".

3. The antithrombin III preparation according to claim 1 or 2 wherein the polyoxyethylene glycol sorbitan alkyl ester is used in an amount of 0.04–20% by weight of antithrombin III.

4. A kit comprising two containers, a first container having therein a lyophilized powder of antithrombin III and a second container having therein a solvent for the said powder, characterized in that a polyoxyethylene glycol sorbitan alkyl ester is added to either or both of the said powder and the said solvent.

5. The kit according to claim 4 wherein the solvent is distilled water for injection.

6. The kit according to claim 4 wherein the containers for the powder and the solvent are vials.

* * * * *